US006844162B1

(12) United States Patent
Smith et al.

(10) Patent No.: US 6,844,162 B1
(45) Date of Patent: Jan. 18, 2005

(54) ASSAYS FOR TSH RECEPTOR AUTOANTIBODIES

(75) Inventors: Bernard Rees Smith, Cardiff (GB); Jane Sanders, Cardiff (GB); Jadwiga Furmaniak, Cardiff (GB)

(73) Assignee: RSR Limited, Cardiff (GB)

( * ) Notice: Subject to any disclaimer, the term of this patent is extended or adjusted under 35 U.S.C. 154(b) by 0 days.

(21) Appl. No.: 09/494,751

(22) Filed: Jan. 31, 2000

Related U.S. Application Data (63) Continuation-in-part of application No. PCT/GB99/01774, filed on Jun. 4, 1999.

(30) Foreign Application Priority Data

| Jun. 6, 1998 | (GB) | ............................................. 9812146 |
| Apr. 28, 1999 | (GB) | ............................................. 9909661 |

(51) Int. Cl.[7] ............................................. G01N 33/53
(52) U.S. Cl. ........................ 435/7.1; 435/7.5; 435/7.7; 435/7.79; 435/7.72; 435/7.93; 435/7.95; 436/518; 436/525; 436/526; 436/527; 436/528; 436/531; 436/535; 436/545; 436/546; 436/548; 436/164; 436/808; 436/172; 436/804
(58) Field of Search .......................... 435/7.1, 7.5, 7.7, 435/7.73, 7.72, 7.93, 7.95; 436/518, 525, 526, 527, 528, 531, 535, 545, 546, 548, 164, 808, 172, 804, 543, 598

(56) References Cited

U.S. PATENT DOCUMENTS

| 4,244,940 | A | * | 1/1981 | Jeong et al. |
| 4,472,508 | A | * | 9/1984 | Ingbar |
| 4,609,622 | A | * | 9/1986 | Kohn et al. |
| 5,578,496 | A | * | 11/1996 | Atassi et al. |
| 5,614,363 | A | * | 3/1997 | Cone |
| 5,639,627 | A | * | 6/1997 | Tanaka |
| 5,705,400 | A | * | 1/1998 | Furmaniak-Wehr |
| 5,744,348 | A | * | 4/1998 | Cone |
| 5,814,461 | A | * | 9/1998 | Bergmann et al. |
| 5,919,632 | A | * | 7/1999 | Bergmann |
| 6,066,475 | A | * | 5/2000 | Maclaren et al. |
| 6,261,800 | B1 | * | 7/2001 | Nikolics et al. |
| 6,284,491 | B1 | * | 9/2001 | Wondisford et al. |

FOREIGN PATENT DOCUMENTS

| DK | WO 98/20343 | * | 5/1998 |
| DK | WO 01/27634 A2 | * | 4/2001 |
| EP | 0719858 | | 12/1995 |
| WO | WO 90/13643 | | 11/1990 |
| WO | 9402748 | | 8/1994 |
| WO | WO 97/00447 | | 1/1997 |
| WO | WO 98/26294 | | 6/1998 |

OTHER PUBLICATIONS

Sanders et al. The Interaction of TSH Receptor Autoantibodies with 125I labeled TSH receptor. 1999, 84(10), 3797–3802.*

(List continued on next page.)

*Primary Examiner*—Christopher L. Chin
*Assistant Examiner*—Pensee T. Do
(74) *Attorney, Agent, or Firm*—Merchant & Gould P.C.

(57) ABSTRACT

A method and kit for monitoring autoantibodies to thyroid stimulating hormone (TSH) receptor in a sample of body fluid, which employs the steps of:
(i) incubating TSH receptor with a sample of body fluid;
(ii) reacting the incubated sample of body fluid with at least one binding agent which is capable of binding to the TSH receptor in competitive reaction with TSH receptor autoantibodies (TRAb), or in a case where TSH receptor is complexed to labelled antibody, reacting the sample of body fluid with at least one binding agent which can bind to TRAb in such a way as not substantially to interfere with binding of the TRAb to the TSH receptor; and
(iii) detecting bound TRAb in the reacted incubated sample of body fluid.

2 Claims, 3 Drawing Sheets

OTHER PUBLICATIONS

Evans, C. et al., "Development Of A Luminescent Bioassay For Thyrotropin–Receptor Antibodies," *J. Endocrinol. Invest. 21*, (Suppl. to No. 4), Abstract, 1 pg. (1998).

Furmaniak, J. et al., "Immunity to the thyroid–stimulating hormone receptor," *Springer Semin Immunopathol.*, vol. 14, pp. 309–321 (1993).

Ludgate, M. et al., "Use of the recombinant human thyrotropin receptor (TSH–R) expressed in mammalian cell lines to assay TSH–R autoantibodies," *Mol. Cell. Endocrinol.*, Abstract from vol. 73, No. 1, 1 pg. (1990).

Matsuba, T. et al., "Expression of recombinant human thyrotropin receptor in myeloma cells," *J. Biochem.*, Abstract from vol. 118, No. 2, 1 pg. (1995).

Miura, S. et al., "Fundamental and clinical evaluation of TSH receptor antibody (TRAb) assay kit," *Igaku to Yakugaku*, Abstract from vol. 30, No. 2, 1 pg. (1993).

Morganthaler, N. et al., "Application of affinity immobilized human recombinant TSH–receptor for the routine measurement of autoantibodies in patients with Graves' disease," *J. Endocrinol. Invest. 21*, (Suppl. to No. 4), Abstract, 1 pg. (1998).

Oda, Y. et al., "Binding characteristics of antibodies to the TSH receptor," *Journal of Molecular Endocrinology*, vol. 20, pp. 233–244 (1998).

Prentice, L. et al., "Comments: Thyrotropin (TSH) Receptor Autoantibodies Do Not Appear to Bind to the TSH Receptor Produced in an in Vitro Transcription/Translation System," *Journal of Clinical Endocrinology and Metabolism*, vol. 82, No. 44, pp. 1288–1292 (1997).

Sanders, J. et al., "Understanding the thyrotropin receptor function–structure relationship," *Baillière's Clinical Endocrinology and Metabolism*, vol. 11, No. 3, pp. 451–479 (Oct. 1997).

Southgate, K. et al., "A Receptor Assay For The Measurement Of TSH Receptor Antibodies In Unextracted Serum," *Clinical Endocrinology*, vol. 20, pp. 539–548 (1984).

\* cited by examiner

ASSAYS FOR TSH RECEPTOR AUTOANTIBODIES

CROSS REFERENCE TO RELATED APPLICATION

The present application is a continuation in part of International Patent Application PCT/GB99/01774 filed on 4th Jun. 1999 by the same applicants as the present invention.

BACKGROUND OF THE INVENTION

The present invention is concerned with assays (kits and analytical methods) for detecting or monitoring TSH Receptor Autoantibodies.

The hyperthyroidism which is associated with Graves' disease is known to be due to autoantibodies to the thyroidal receptor for thyroid stimulating hormone (TSH). The autoantibodies bind to the receptor and mimic the actions of the natural ligand (TSH), thereby causing the gland to produce high levels of thyroid hormones (as described in Endocrine Reviews 1988, Vol 9, No. 1, pages 106 to 117).

The detection or monitoring of TSH receptor autoantibodies (TRAb) is important in the diagnosis and management of Graves' disease and currently two types of assay are used, namely:

(a) competitive binding assays which measure the ability of TRAb to inhibit the binding of $^{125}$I-labelled TSH to preparations of TSH receptor; and (b) bioassays which measure the ability of TRAb to stimulate thyroid cells (or other cells transfected with the TSH receptor gene) in culture.

Currently, competitive binding assays (type (a) above) are more widely used, because bioassays of the type mentioned in (b) above are expensive, time-consuming, require highly skilled staff and are unsuitable for wide routine use. In current competitive binding assays, test serum samples (50 $\mu$l) are generally incubated with detergent solubilized porcine TSH receptor (50 $\mu$l). TRAb present in the test sera bind to the TSH receptor during this incubation. $^{125}$I-labelled TSH is then added and the incubation continued. During this second incubation, the labelled TSH binds to TSH receptors not already occupied by TRAb. Finally, $^{125}$I-labelled TSH bound to the receptor is separated from free labelled TSH by addition of polyethylene glycol (PEG), which precipitates the receptor bound TSH but not the free TSH. The radioactivity in the precipitates (separated by centrifugation) is then counted. In the assay, TRAb in test samples inhibits the binding of labelled TSH to the TSH receptor and this results in a lowering of the radioactivity in the precipitates. Assay results can be expressed as an index of inhibition of labelled TSH binding or by use of a set of assay calibrators.

The main limitations of this conventional assay are as follows:

(a) The assay measures competition between labelled TSH and the TSH receptor and may not detect TRAb which bind well to the receptor but in such a way as not to inhibit TSH binding strongly.

(b) The assay uses polyethylene glycol to separate receptor bound and free labelled TSH. This results in co-precipitation of all the serum immunoglobulins and the formation of a relatively large pellet. Although the pellet can be counted for radioactivity, it is not a suitable preparation to detect TSH (or other proteins or peptides) labelled with non-radioactive substances such as enzymes or chemiluminescent materials. This is because the serum components in the pellet interfere with such processes as light emission. In addition, the use of PEG precipitation necessitates the use of centrifugation and this is a time-consuming and cumbersome procedure unsuitable for automation.

Published patent specification EP0719858A describes an assay method for TSH receptor autoantibodies, where TSH receptor is bound to a solid phase either directly or via anti-TSH receptor antibody. A method for determination of TSH receptor autoantibodies present in patient serum is also described in published patent specification WO95/06258.

OBJECTS OF THE INVENTION

It is an object of the present invention to provide an improved assay for TRAb of the competitive binding type.

It is a further object of the present invention to provide an improved assay kit of the competitive binding type for monitoring TRAb present in a sample of body fluid.

It is a further object of the present invention to provide an improved TRAb assay of the direct binding type, in which a direct interaction between the receptor and TRAb is used.

It is a further object of the present invention to provide an improved assay kit of the direct binding type for monitoring TRAb present in a sample of body fluid.

SUMMARY OF THE INVENTION

The present invention provides a method of monitoring autoantibodies to thyroid stimulating hormone (TSH) receptor in a sample of body fluid, comprising, in the following order, the steps of:

(a) providing (i) porcine TSH receptor or a fragment thereof immobilized to a solid phase, or (ii) TSH receptor which is complexed to a labelled antibody;

(b) incubating the TSH receptor with a sample of body fluid;

(c) reacting the incubated sample of body fluid containing the TSH receptor with at least one binding agent which is capable of binding to the TSH receptor in competitive reaction with TSH receptor autoantibodies (TRAb), or when the TSH receptor is (ii), reacting the sample of body fluid, during or after step (b), with at least one binding agent which can bind to TRAb in such a way as not substantially to interfere with binding of the TRAb to the TSH receptor; and (d) qualitatively or quantitatively detecting bound TRAb in the reacted incubated sample of body fluid.

The sample of body fluid typically comprises blood, plasma or serum.

The invention comprises the use of antibodies in order to label or immobilize a TSH receptor, the immobilized or labelled TSH receptor being such that it retains its ability to bind TSH and/or TRAb.

The present invention preferably concerns the use of a monoclonal (or polyclonal) antibody to the TSH receptor, which is bound strongly to the receptor at a site distinct from the part of the receptor which binds TSH and TRAb. The antibody can bind to the receptor strongly at the same time as TSH or TRAb and can be used to alleviate many of the limitations of the current TRAb assay method.

In a first embodiment of the invention, the antibody can be immobilized on a solid phase (such as a plastic tube or plastic plate, or magnetic or non-magnetic particles) using standard procedures. This solid phase can then be used instead of PEG to separate labelled TSH bound to the TSH receptor from free labelled TSH. The TSH (or similar ligand) can be labelled with isotopic or non-isotopic labels.

There are several applications of this first embodiment, of which the following are schematic examples:

(i) TSH receptor + labelled TSH ⟶ TSH receptor-labelled TSH

□-Ab-TSH receptor-labelled TSH

(ii) □-Ab-TSH receptor + labelled TSH ⟶ □-Ab-TSH receptor-labelled TSH

Form this complex first    binding inhibited by TRAb (iii) In (i) and (ii) above, the receptor Ab can be bound indirectly to the solid phase. For example, the Ab can be biotinylated and reacted with the solid phase which contains avidin or streptavidin:

(a)

Bi-Ab-TSH receptor + labelled TSH ⟶ Bi-Ab-TSH receptor-labelled TSH complex □-Avidin-Bi-Ab-TSH receptor-labelled TSH (b)

□-Avidin-Bi-Ab-TSH receptor + labelled TSH ⟶ □-Avidin-Bi-Ab
Form this complex first

TSH receptor

| labelled TSH

In a second embodiment of the invention, the antibody can be labelled directly with an isotopic label such as $^{125}$I, or with a non-isotopic label such as an enzyme, dye, or chemiluminescent compound. Alternatively, the antibody may be labelled indirectly using, for example, the avidin-biotin system. The labelled antibody can then be used to label the TSH receptor itself and this complex of receptor and antibody can then be used to detect and/or monitor TRAb (either qualitatively or quantitatively). Examples of this approach are described schematically as follows:

(i)

□-protein A-TRAb

In this system, increasing amounts of TRAb in a test sample will result in increasing amounts of labelled Ab in the final complex.

(ii) This example depends on the coupling of TSH (or similar ligand) directly or indirectly to a solid phase (□-TSH) receptor labelled with the antibody (which is itself labelled with an isotopic or non-isotopic label), which can bind to this immobilized TSH (or similar ligand). This binding will be inhibited by TRAb, as illustrated below:

□-TSH + TSH receptor-labelled Ab ----▶ □-TSH-TSH receptor
immobilized TSH binding inhibited    labelled Ab
by TRAb The schemes described above with reference to the first and second embodiments of the invention illustrate certain advantages of the present invention. The immobilized antibody may be used to label or immobilize the TSH receptor in such a way that the receptor retains its ability to bind TSH and/or TRAb. Alternatively, the immobilized antibody may be used for the monitoring of TRAb (or other ligands which interact with the TSH receptor) in patient sera, or for purification of the TSH receptor.

In particular, the ability to label the TSH receptor using the antibody permits monitoring of the direct interaction of TRAb with the TSH receptor as in the second embodiment of the invention described above. Furthermore, the present invention allows the immobilization of the receptor before, during, or after interaction with TSH and TRAb. This ability to immobilize the receptor can be used to create new TRAb assays which do not depend on PEG and/or isotopic labels. Such assays may be suitable for automation and immunochromatographic systems.

The TSH receptor (TSHR) is present in very low numbers on the surface of thyrocytes (about $10^3$ receptors per cell) which has made the receptor very difficult to purify from native sources (as described in "Baillière's Clinical Endocrinology and Metabolism", 1997, Vol II, pages 451 to 474—Sanders).

In contrast, recombinant TSHR can be expressed in mammalian cells (for example, in Chinese hamster ovary (CHO) cells) at much higher levels of about $10^5$–$10^6$ receptors per cell (Sanders). In addition, recombinant TSHR preparations produced in non-thyroid cells are not contaminated with other thyroid autoantigens such as thyroglobulin or thyroid peroxidase (Springer Seminars in Immunopathology, 1993, pages 309–318—Furmaniak).

Recombinant TSHR preparations produced in mammalian cells are the only ones which show TSH and TRAb binding characteristics similar to that of the native receptors. Such binding characteristics are not, for example, produced in yeast, insect cells or bacteria. This is because of a very complex relationship between the TSHR's structure and the TSH/TRAb binding sites. The TSHR's post-translational processing and folding of the "mature" protein is best achieved in the mammalian cell environment (see Sanders).

Purification of large amounts of recombinant TSHR from mammalian cells with its TSH and TRAb binding activities intact has not been reported. One of the major problems is loss of TSH/TRAb binding activity following binding with mouse monoclonal antibodies interacting with the extracellular part of the TSHR (Sanders). Also, to date, development of new and convenient strategies for routine measurement of TRAb has not been successful.

EXAMPLES

Preferred features of the present invention are illustrated by the following non-limiting detailed worked examples.

1. Cloning of Porcine TSHR cDNA

RNA was extracted from porcine thyroid tissue using the guanidinium thiocyanate-phenol chloroform method (Chomczynski and Sacchi, Anal. Biochem. Vol 162. 1987, pages 156 to 59). mRNA was purified from total RNA using a Dynal bead mRNA purification kit (Dynal, Wirral L62 SAZ UK). This mRNA was used to make a cDNA library using ZapExpress cDNA Gigapack Cloning Kit III (Strategene Ltd., Cambridge CB4 4DF UK). Four degenerate oligonucleotides were made to the known TSHR sequences (mouse, rat, human, dog and bovine) and two fragments of porcine TSHR amplified using PCR. These were sequenced to verify their homology with TSHR cDNA and used to screen the cDNA library for full-length porcine TSHR clones. Three full-length clones were obtained and fully sequenced.

2. Expression of Porcine Recombinant TSHR Protein in CHO Cells

An ATG start codon in the 5' untranslated region (5' UTR) of the full-length pTSHR cDNA was removed by PCR and the cDNA cloned into pcDNA 3.1 (+) (Invitrogen BV, 9351 NV Leek, The Netherlands). DNA encoding the full-length TSHR was transfected into CHO cells (CHO-KI from ECACC, Porton Down SP4 OJG UK) by electroporation. Clones expressing TSHR were detected using $^{125}$I-TSH binding directly to cells growing on 24-well plates. The clones showing highest TSH binding were expanded and recloned twice by limiting dilution. One stable cell line expressing about $4\times10^5$ TSHR per cell was chosen for expansion and production of recombinant TSHR.

3. Preparation of Detergent Solubilized Recombinant Porcine TSHR

CHO cells expressing TSHR were grown to confluence, detached from roller bottles and the cell pellet washed with ice-cold 50 mM NaCl, 10 mM Tris-HCl, pH 7.5 containing 1 mM phenylmethylsulfonylfluoride (PMSF), then homogenized in the same buffer. The cell membranes after centrifugation at 12000 g for 30 min at 4° C. were solubilized in the same buffer (4 ml of buffer for approximately $4\times10^8$ cells) as used for homogenization except for addition of 1% Triton X-100. The solubilized receptor preparations were centrifuged at 90,000 g for two hours at 4° C. and the supernatant stored at −70° C.

4. Expression of the C-terminal End of the Porcine TSHR Protein

The expression in *Escherichia coli* as a fusion protein with glutathione S-transferase (GST) was carried out using standard protocols (as described in Journal of Molecular Endocrinology (1998) Vol 20, pages 233–244—Oda). The 3' end of cDNA (1809 to 2295 bp) coding for the last 160 amino acids was cloned in frame with the GST fusion protein in pGEX2T vector (Pharmacia Biotech, St. Albans AL1 3AW UK). An overnight culture of *E. coli* (strain UT580) transformed with pGEX-2T/TSHR plasmids was diluted 1/5 into 2×YTG medium (16 g Tryptone, 10 g yeast extract, 5 g NaCl, 20 g glucose per liter, pH 7.0), incubated for 3 hours at 30° C. Thereafter, isopropyl-3-D-thiogalactopyranoside (IPTG) was added to a final concentration of 1 mM in order to induce protein expression, followed by incubation for a further three hours. The bacterial pellets were resuspended in PBS (8 g NaCl, 0.2 g KCl, 1.44 g $Na_2HPO_4$ and 0.24 g $KH_2PO_4$ per liter, pH 7.4) containing 1% Triton X-100 and sonicated three times for one minute on ice. The inclusion bodies were pelleted, washed in 4M urea, solubilized in 8M urea and separated on 9% polyacrylamide gels (SDS-polyacrylamide electrophoresis, SDS-PAGE) under reducing conditions. The TSHR/GST fusion proteins (mol. wt. 44 kDa) were electroeluted from polyacrylamide gel slices in 0.1M $NaHCO_3$ and 0.1% SDS pH 7.8, dialyzed against 50 mM Tris-HCl pH 8.0 and stored in aliquots at −70° C.

5. Preparation and Purification of Monoclonal Antibodies to the Porcine TSHR

Electroeluted TSHR/GST protein was used to immunize BALB C mice (50 µg per mouse per injection) until the titer of antibody to the TSHR was high. The TSHR antibody level in mouse sera was tested using immunoprecipitation assay based on $^{35}$S-labelled TSHR produced in an in vitro transcription/translation system (see the method described in Journal of Clinical Endocrinology and Metabolism, Vol 82 (1997) No. 4, pages 1288–1292—Prentice). Mouse spleen cells were fused with mouse myeloma cell line (X63-Ag8.653 from ECACC) and cloned to produce stable hybridomas secreting the TSHR antibody using standard techniques (Oda). The antibody 4E31 was found to precipitate $^{35}$S-TSHR in the immunoprecipitation assay and to react well with the TSHR in Western blotting analysis. 4E31 was purified from hybridoma culture supernatants by chromatography on a Prosep-A (Bioprocessing, Consett DH8 6TJ UK) column. $Fab_2$ fragments were obtained following digestion with pepsin (pepsin concentration of 1 mg/ml in 70 mM sodium acetate, 50 mM NaCl pH 4.0, IgG to enzyme ratio of 5:1) and chromatography on Prosep A to adsorb intact IgG. 4E31 $Fab_2$ preparations of about 1 mg/ml were stored at −70° C. in aliquots.

6. TSH Receptor Binding Characteristics of the 4E3 1 Antibody

Solubilized recombinant porcine TSH receptor was incubated with $^{125}$I-labelled TSH to form a $^{125}$I-labelled TSH-TSH receptor complex. The 4E31 IgG (or control IgG) was immobilized by linking it to magnetic latex beads and these beads (100 µl; 1 µg of 4E31) were incubated with the preformed $^{125}$I-labelled TSH-TSH receptor complex (100 µl). After 1 hr at 37° C., the beads were separated on a magnet, washed and counted for $^{125}$I. A sample of the $^{125}$I-labelled TSH-TSH receptor complex was precipitated with PEG to determine the amount of free labelled TSH present. Table 1 shows the results obtained:

TABLE 1

| Sample | cpm Bound to Beads |
|---|---|
| 4E31 IgG beads plus:- | |
| (a) labelled TSH-TSH receptor complex | 16,374 |
| (b) labelled TSH only | 2,118 |
| Control IgG beads plus labelled TSH-TSH receptor complex | 2,433 |
| Labelled TSH-TSH receptor complex precipitated by PEG | 16,499 |
| Total cpm in 100 μl of labelled complex | 37,073 |

(Control IgG used was a mouse monoclonal antibody to glutamic acid decarboxylase)

These studies indicated clearly that 4E31 could bind to the TSH receptor at the same time as TSH. Further, 4E31 coupled to a solid support could be used to separate TSH bound to the TSH receptor from free TSH with results similar to those obtained with PEG. Table 2 shows that in the presence of individual healthy human donor sera, about 55% of the labelled TSH added bound to tubes coated with 4E31 and recombinant porcine TSH receptor (according to the first embodiment of the invention, scheme ii above). Similar binding was observed in the case of sera from patients with Hashitmoto's thyroiditis and patients with systemic lupus erythematosus (SLE). However with sera from the 5 patients with Graves' disease, there was markedly less labelled TSH binding (about 35%). All 5 sera contained readily detectable amounts of TSH receptor autoantibody as judged by inhibition of TSH binding to native porcine TSH receptor and separation of receptor bound and free TSH with PEG.

TABLE 2

Binding of labelled TSH to plastic tubes coated with 4E31 (Fab)$_2$ followed by recombinant porcine TSH receptor - effect of different sera.

| | | inhibition of TSH binding (%) | |
|---|---|---|---|
| Sample | cpm bound | coated tube method (recombinant receptor) | PEG method (native receptor) |
| Individual normal sera:- | | | |
| 1 | 15,171 | | |
| 2 | 15,209 | | |
| 3 | 15,480 | | |
| 4 | 14,768 | | |
| 5 | 15,496 | | |
| Individual Graves' sera:- | | | |
| 1 | 10,132 | 34 | 27 |
| 2 | 9,575 | 37 | 31 |
| 3 | 12,495 | 18 | 21 |
| 4 | 11,478 | 25 | 11 |
| 5 | 9,163 | 40 | 48 |
| Individual Hashimoto sera:- | | | |
| 1 | 14,659 | | |
| 2 | 15,215 | | |
| 3 | 14,603 | | |
| 4 | 15,026 | | |
| 5 | 15,370 | | |
| Individual SLE sera:- | | | |
| 1 | 15,711 | | |
| 2 | 15,261 | | |

TABLE 2-continued

Binding of labelled TSH to plastic tubes coated with 4E31 (Fab)$_2$ followed by recombinant porcine TSH receptor - effect of different sera.

| | | inhibition of TSH binding (%) | |
|---|---|---|---|
| Sample | cpm bound | coated tube method (recombinant receptor) | PEG method (native receptor) |
| 3 | 15,091 | | |
| 4 | 15,386 | | |
| 5 | 15,403 | | |
| Total cpm | 27,420 | | |

Table 3 shows results similar results with tubes coated with native (i.e. non-recombinant) porcine TSH receptor via E31. Again, the results obtained with the coated tube assay are similar to those obtained with the PEG separation method.

TABLE 3

Binding of labelled TSH to plastic tubes coated with 4E31 (Fab)$_2$ followed by native detergent solubilized porcine TSH receptor.

| | inhibition of TSH binding (%) with:- | |
|---|---|---|
| Sample | native porcine TSH receptor bound to plastic tubes (via 4E31 (Fab)$_2$) | native porcine TSH receptor PEG precipitation assay |
| Individual normal sera:- | | |
| a | 1.5 | −0.62 |
| b | 2.2 | 3.2 |
| c | −5.0 | 3.9 |
| d | 1.8 | 3.2 |
| Graves sera:- | | |
| 6 | 74 | 71 |
| 7 | 75 | 72 |
| 8 | 81 | 76 |
| 9 | 70 | 73 |
| 10 | 77 | 88 |
| 11 | 66 | 83 |
| 12 | 88 | 72 |
| 13 | 80 | 76 |
| 14 | 57 | 70 |
| 15 | 90 | 86 |
| 16 | 55 | 72 |
| 17 | 81 | 68 |

The inhibiting effect on $^{125}$I-TSH binding shown in tables 2 and 3 was dependent on the concentration of TRAb in the serum. As shown in Table 4, increasing amounts of TRAb standard preparation (thyroid stimulating antibody 1st International Standard 90/672) had a dose dependent effect on TSH binding inhibition.

TABLE 4

| TRAb standard dilution (mu/ml) | native porcine TSH receptor (PEG separation method) - inhibition of TSH binding (%) | 4E31/recombinant porcine TSH receptor coated tubes - inhibition of TSH binding (%) |
|---|---|---|
| 0 | 0 | 0 |
| 1.25 | 5.1 | 5.1 |
| 2.5 | 9.9 | 12.0 |
| 5 | 16.2 | 17.0 |
| 10 | 28.4 | 31.7 |

TABLE 4-continued

| TRAb standard dilution (mu/ml) | native porcine TSH receptor (PEG separation method) - inhibition of TSH binding (%) | 4E31/recombinant porcine TSH receptor coated tubes - inhibition of TSH binding (%) |
|---|---|---|
| 20 | 44.5 | 51.6 |
| 40 | 69.1 | 74.8 |

Direct Precipitation of $^{125}$I-4E31 Fab$_2$-TSH Complexes

Another example of the invention (according to the second embodiment of the invention, scheme (i) above) is an assay in which 4E31 (Fab)$_2$ is labelled with $^{125}$I and reacted with the TSH receptor. This complex is then incubated with TSH receptor autoantibodies in patients' sera and the resulting termolecular complex precipitated by addition of solid phase protein A. An example is shown in Table 5.

TABLE 5

Reaction between recombinant porcine TSH receptor labelled with $^{125}$I-4E31 (Fab)$_2$ and TSH receptor autoantibodies.

| Sample | cpm bound |
|---|---|
| Labelled receptor plus:- | |
| Individual normal serum:- | |
| e | 1,994 |
| f | 2,041 |
| 90/672 reference material (mU/ml): | |
| 1.25 | 2,715 |
| 2.5 | 2,958 |
| 5 | 3,358 |
| 10 | 4,202 |
| 20 | 5,868 |
| 40 | 8,949 |
| Graves' serum:- | |
| 18 | 12,326 |
| 19 | 13,225 |
| Total cpm | 48,428 |

Graves' sera 18 and 19 gave TSH binding inhibition values of 31% and 73% respectively in the PEG precipitation method using native porcine TSH receptor. 4E31 could be labelled with biotin, bound to streptavidin coated tubes and then reacted with porcine TSH receptor—see the first embodiment of the invention, Scheme (iii) b. Receptor immobilized in this way readily bound $^{125}$I-labelled TSH and this binding was inhibited by TSH receptor autoantibodies in patient sera. An example is shown in Table 6.

TABLE 6

Labelled TSH binding to TSH receptor - bound to streptavidin coated tubes via biotinylated 4E31 (Fab)$_2$ and effect of TRAb.

| Serum Sample | $^{125}$I-labelled TSH bound (cpm) |
|---|---|
| Individual healthy normal sera:- | |
| g | 12,225 |
| h | 12,164 |
| TRAb positive Graves' sera:- | |
| 20 | 2,971 |
| 21 | 7,400 |
| Total cpm | 27,339 |

BRIEF DESCRIPTION OF THE DRAWINGS

Features of the present invention and results obtained will now be described and illustrated with reference to the drawings, in which.

Figure 1:
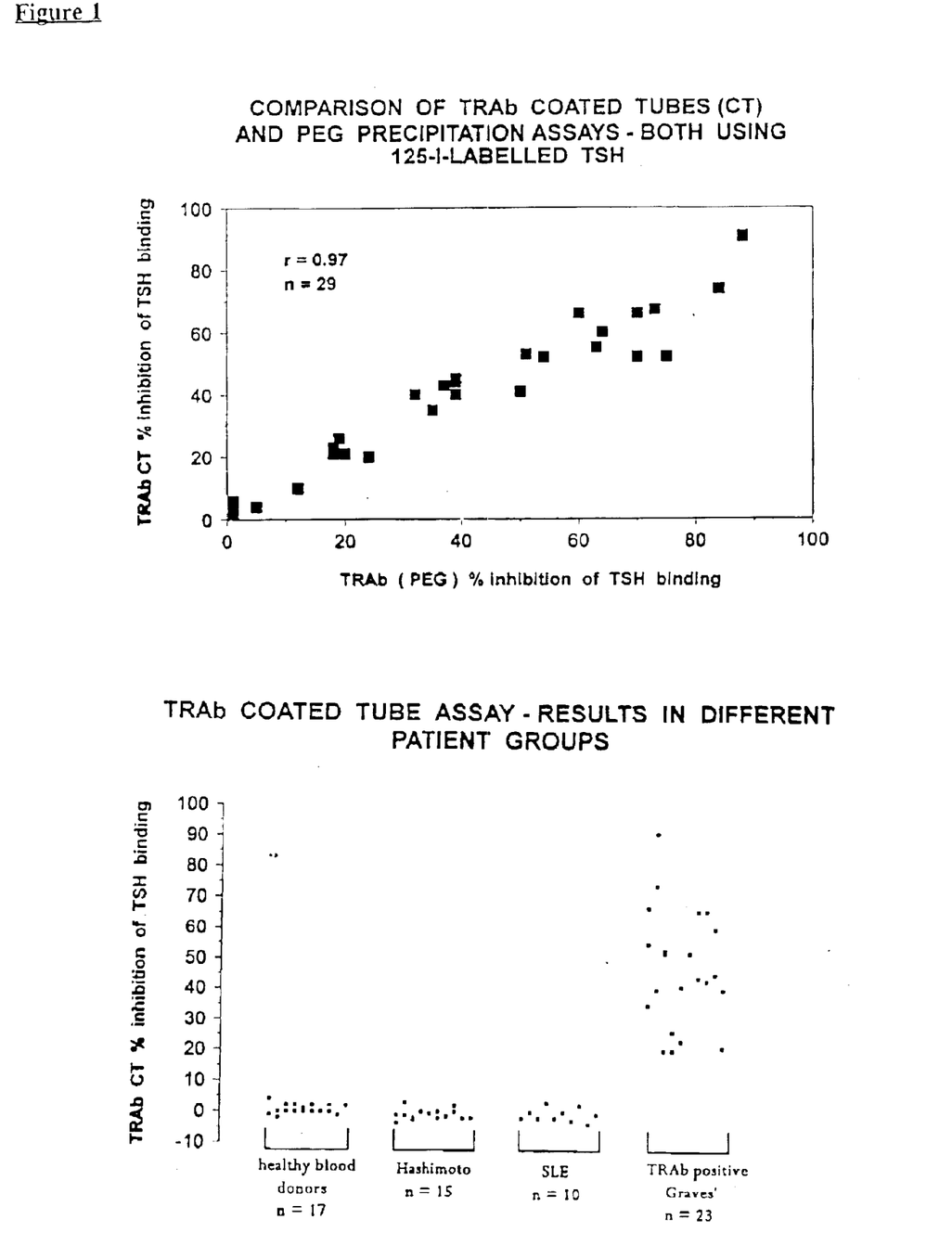
FIG. 1 illustrates the correlation between results using a method of monitoring autoantibodies to thyroid stimulating hormone receptor using TRAb coated tubes and a method using PEG precipitation assays, both methods using $^{125}$I-labelled bovine TSH. Furthermore, results in different patient groups with the method using TRAb coated tubes are shown.
Figure 2:
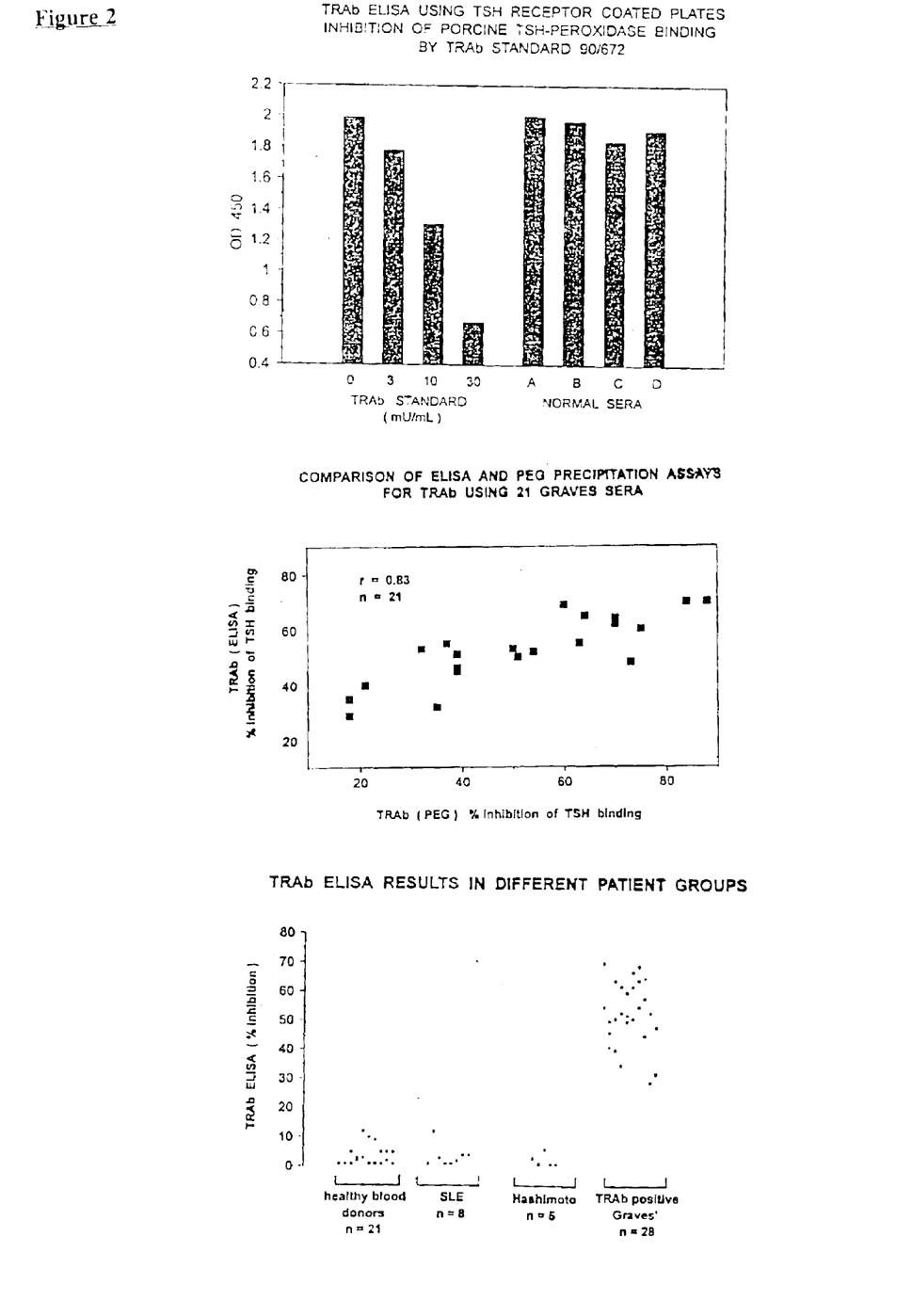
FIG. 2 illustrates results of an ELISA method using TSH receptor coated plates; 2a shows the effect of TRAb standard 90/672 on porcine TSH binding to receptor-coated plates; 2b shows a comparison of an ELISA method and a PEG precipitation assay; and results in different patient groups with a TRAb ELISA method using bovine TSH are shown in 2c.
Figure 3:
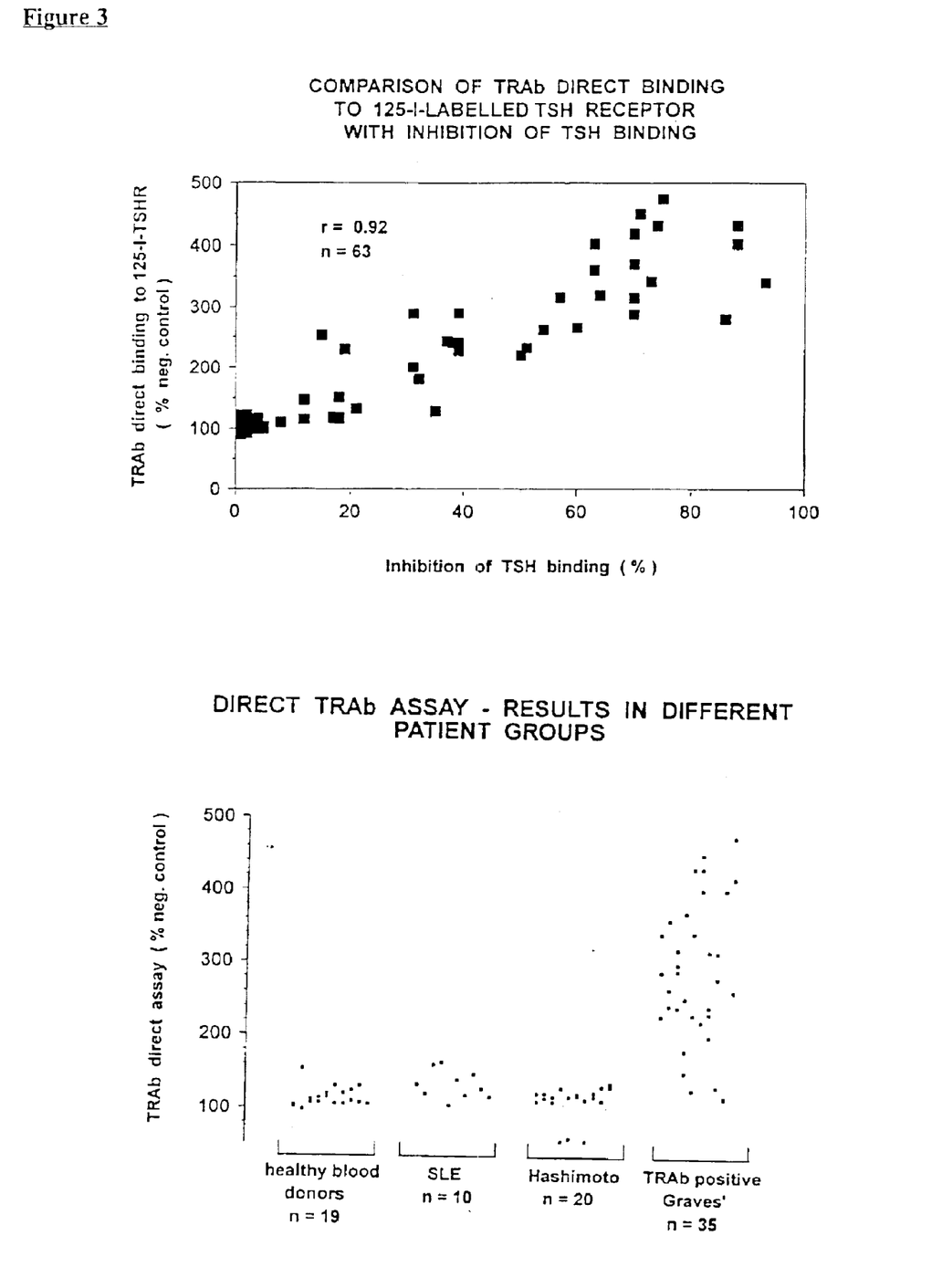
FIG. 3 illustrates the correlation between a conventionally used TRAb assay method and a direct precipitation assay method according to the invention. Furthermore, results in different groups with a direct TRAb assay are shown.

What is claimed is:

1. A kit for use in screening a sample of body fluid for autoantibodies to the TSH receptor, which kit comprises.
    (a) at least one antibody, or fragment thereof that binds to an epitope present in, or derived from, the last 160 amino acids of the TSH receptor, with which autoantibodies to the TSH receptor do not interact;
    (b) a source of TSH comprising (i) a first binding region comprising said epitope with which said antibody of (a) binds, and which is present in, or is derived from, the last 160 amino acids of the TSH receptor, and (ii) a second binding region comprising at least one epitope with which autoantibodies to the TSH receptor interact, said first and second binding regions being such that said TSH receptor retains its ability to bind TSH receptor autoantibodies in addition to binding with said antibody of (a), whereby said TSH receptor can concurrently bind:
    said antibody of (a) at said epitope of said first binding region of said TSH receptor; and TSH receptor autoantibodies, when present in said sample of body fluid being screened, at said epitope of said second binding region of said TSH receptor;
    (c) means for contacting said TSH receptor of (b) with:
    said sample of body fluid being screened; and
    said antibody of (a);
    whereby said contracting means allow said antibody of (a) to bind said epitope of said first binding region of said TSH receptor of (b), and said autoantibodies when preset in said sample of body fluid being screened to concurrently bind with said epitope of said second binding region of said TSH receptor of (b); and
    (d) means for monitoring binding of said autoantibodies and said TSH receptor of (b), so as to provide an indication of the presence of TSH receptor autoantibodies in said sample of body fluid being screened.

2. A kit for use in screening a sample of body fluid for autoantibodies to the TSH receptor, which kit comprises:
    (a) antibody Mab 4E31, or fragment thereof;
    (b) a source of TSH receptor comprising (i) a first binding region comprising an epitope with which antibody Mab 4E31 of (a) binds, and which is present in, or is derived from, the last 160 amino acids of the TSH receptor, and (ii) a second binding region comprising at least one epitope with which autoantibodies to the TSH receptor interact, said first and second binding regions being such that said TSH receptor retains its ability to bind THS receptor autoantibodies in addition to binding with antibody Mab 4E31 of (a), whereby said TSH receptor can concurrently bind:

antibody Mab 4E31 of (a) at said epitope of said first binding region of said TSH receptor; and TSH receptor autoantibodies, when present in said sample of body fluid being screened, at said epitope of said second binding region of said TSH receptor;

(c) means for contacting said TSH receptor of (b) with:

said sample of body fluid being screened; and antibody Mab 4E31 of (a);

whereby said contacting means allow antibody Mab 4E31 of (a) to bind said epitope of said first binding region of said TSH receptor of (b), and said autoantibodies when present in said sample of body fluid being screened to concurrently bind with said epitope of said second binding region of said TSH receptor of (b); and (d) means for monitoring binding of said autoantibodies and said TSH receptor of (b), so as to provide an indication of the presence of TSH receptor autoantibodies in said sample of body fluid being screened.

* * * * *

UNITED STATES PATENT AND TRADEMARK OFFICE
CERTIFICATE OF CORRECTION

PATENT NO. : 6,844,162 B1
DATED : January 18, 2005
INVENTOR(S) : Bernard Rees Smith, Jane Sanders and Jadwiga Furmaniak It is certified that error appears in the above-identified patent and that said Letters Patent is hereby corrected as shown below:

Column 10,
Line 31, -- TSH receptor -- should replace "TSH".
Line 51, -- contacting -- should replace "contracting".
Line 54, -- present -- should replace "preset".

Column 11,
Line 5, -- TSH -- should replace "THS".

Signed and Sealed this

Thirtieth Day of August, 2005

JON W. DUDAS
*Director of the United States Patent and Trademark Office*